Figure 1:
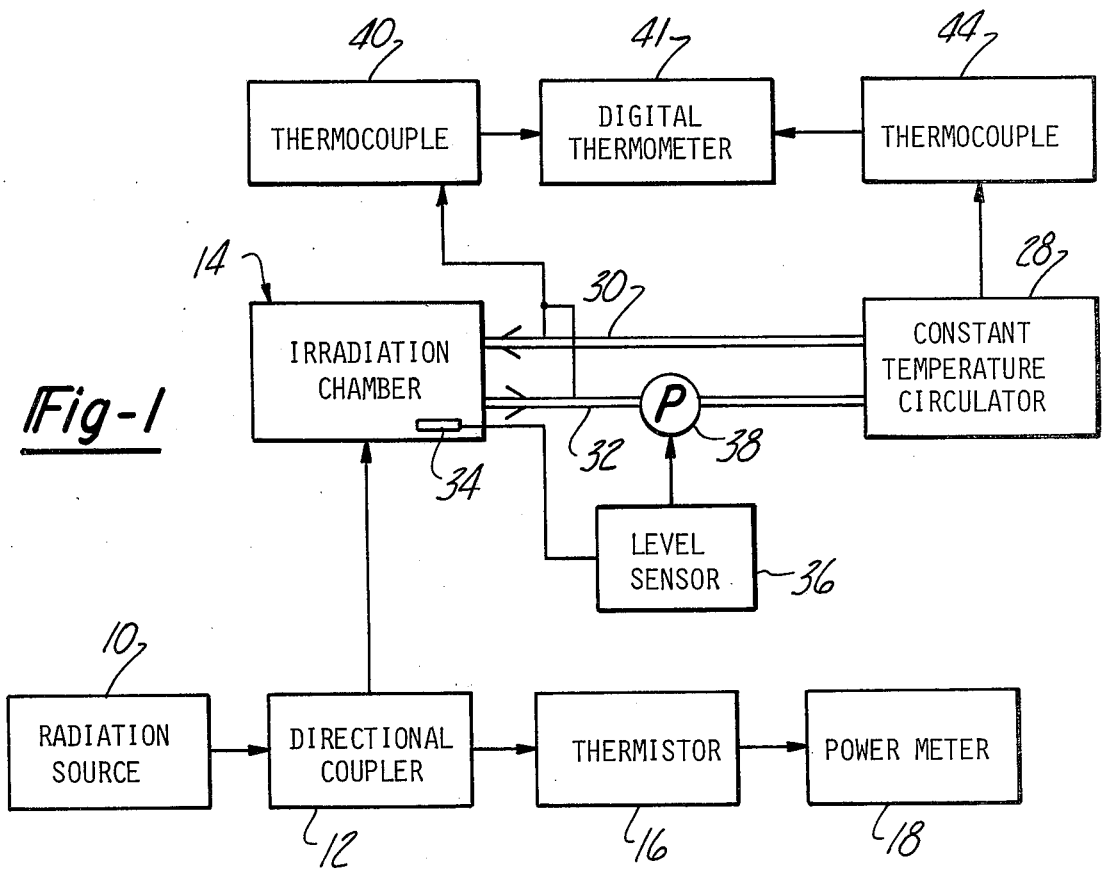

United States Patent [19]

Chen

[11] 4,327,180
[45] Apr. 27, 1982

[54] METHOD AND APPARATUS FOR ELECTROMAGNETIC RADIATION OF BIOLOGICAL MATERIAL

[75] Inventor: Kuo-Chun Chen, Birmingham, Mich.

[73] Assignee: Board of Governors, Wayne State Univ., Detroit, Mich.

[21] Appl. No.: 75,636

[22] Filed: Sep. 14, 1979

[51] Int. Cl.³ .............................................. C12N 13/00
[52] U.S. Cl. ...................................... 435/173; 435/29; 435/287; 435/291; 435/316
[58] Field of Search ................ 435/29, 173, 287, 291, 435/316

[56] References Cited

U.S. PATENT DOCUMENTS 2,196,361  4/1940  Liebesny et al. ..................... 435/173
3,494,723  2/1970  Gray .................................... 435/173
3,660,234  5/1972  Gray .................................... 435/173

Primary Examiner—Alvin E. Tanenholtz
Attorney, Agent, or Firm—Krass, Young & Schivley

[57] ABSTRACT

Living cells suspensed in a saline buffering media are exposed to microwave radiation without raising the temperature of the cells, to study the non-thermal effects of radiation on the cells, in an apparatus which includes a vertically disposed microwave waveguide having a partitioned end filled with a temperature controlled liquid solution. The sample is contained in a micropipette which projects across the width of the waveguide through the solution. The radiation projected through the waveguide and into the solution is measured.

14 Claims, 2 Drawing Figures

METHOD AND APPARATUS FOR ELECTROMAGNETIC RADIATION OF BIOLOGICAL MATERIAL

BACKGROUND OF THE INVENTION

1. Field of the Invention

This invention relates to a method of irradiating living cells without increasing their temperature and to apparatus for practicing the method which includes a temperature controlled liquid chamber disposed within a waveguide and having a sample container projecting through the container.

2. Summary of the Prior Art

When in vitro biological material such as cells, tissues and organs, are exposed to electromagnetic radiation, changes are effected in the biological material. At least part of these changes result from the heating of the material by the incident radiation. While there also may be a direct non-thermal effect of the radiation on the biological material it is difficult to separate the thermal from the direct non-thermal factors and accordingly evidence for involvement of the direct non-thermal factors has not been heretofore convincingly established.

SUMMARY OF THE INVENTION

The present invention allows in vitro biological bodies, such as cells and the like, to be subjected to electromagnetic radiation, and particularly short wavelength radiation such as microwaves and the like, without increasing the temperature of the biological matter so that the non-thermal effect of the radiation may be determined. The method also allows the quantity of radiation to which the biological material is subjected to be precisely measured and the temperature of the material to be precisely controlled.

In the practice of the present invention the electromagnetic radiation is conventionally generated and is directed through an elongated waveguide. The waveguide is preferably aligned with its central axis in a vertical direction. A partition or bulkhead is disposed across the waveguide to form a chamber that is filled with a liquid media suitable for the life support of biological material. The bulkhead is formed of a material that matches the impedance of the chamber to that of the waveguide so that when the chamber is filled with the liquid media substantially all of the radiation passing through the waveguide is absorbed within the media.

The media is maintained at a constant temperature by circulation through suitable temperature modifying apparatus. The in vitro cells are supported in the same media that fills the chamber, within a micropipette that projects into the chamber and is supported parallel to the partition. Heat transfer between the media within the micropipette and the media in the chamber maintains the cells at the same constant temperature as the liquid within the chamber. By measurement of the radiation in the waveguide and the knowledge of the geometry of the device the energy impinging upon the sample may be accurately measured.

Figure 2:
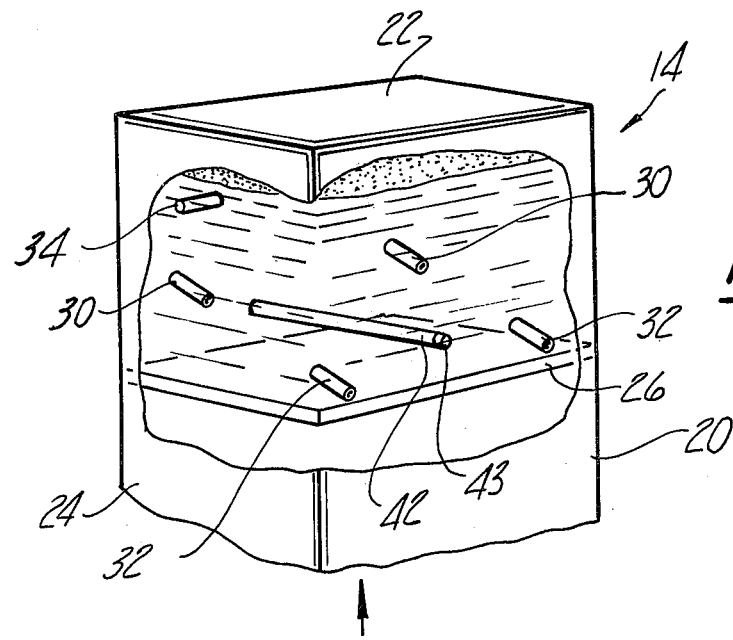

Other objects, advantages and applications of the present invention will be made apparent by the following detailed description of a preferred embodiment of the invention. The description makes reference to the accompanying drawings in which:

FIG. 1 is a block diagram of apparatus representing a preferred embodiment of the invention, which is adapted to practice the method of the present invention; and FIG. 2 is a perspective view, partially broken away for purposes of illustration, of the irradiation chamber of the apparatus of the preferred embodiment of the present invention.

Referring to the drawings, the present invention can be employed with any electromagnetic radiation but is preferably used to study the effects of microwave radiation and accordingly employs a microwave source 10, indicated in FIG. 1, for the radiation. In the preferred embodiment of the invention the source 10 is a commercially available continuous wave magnetron operating at 2450 MHz.

The radiation output of the source is provided to a directional coupler 12. The coupler connects the radiation from the source 10 to a waveguide exposure chamber 14. It also carries a probe which taps off radiation to a thermistor 16 which is in turn coupled to a power meter 18.

The directional coupler 12 may be adjusted so the probe measures the power passing from the magnetron 10 to the waveguide exposure chamber 14 or alternatively the radiation reflected back to the souce from the chamber. In this manner the net radiation incident upon a sample disposed in the chamber may be determined.

The construction of the chamber 14 itself is illustrated in FIG. 2. The chamber is formed of a section of rectangular waveguide 20 which may have an open end 22. The waveguide section is disposed vertically and its lower end 24 connects to the coupler 12. A partition or bulkhead 26 is formed across the chamber and consists of a sheet of dielectric material which acts as a quarter-wavelength matching layer.

The layer 26 makes a fluid seal with the edges of the waveguide and the volume above the layer 26 is filled with a liquid. In the preferred embodiment of the invention the liquid constitutes a phosphate buffered saline solution. The solution is circulated between the chamber 14 and an external container 28, illustrated in FIG. 1, by an inlet pipe 30 and an outlet pipe 32. A liquid level sensing probe 34 is disposed in one sidewall of the chamber and is connected to a liquid sensor 36. The sensor controls a pump 38 disposed in the outlet line to maintain a constant liquid level in the chamber.

A thermocouple 40 may be alternatively connected to either the inlet line 30 or the outlet line 32. Its output is provided to a digital thermometer 41. A second thermocouple 44 is connected to the constant temperature circulator 28 and its output is also provided to the digital thermometer 41. Through appropriate switching (not shown) the digital thermometer 41 may display either the inlet temperature, the outlet temperature, or the temperature of the circulator.

The constant temperature circulator 28 includes suitable cooling means which maintains the temperature of the liquid passing to the chamber 14 through the inlet at a preset temperature.

A pipette 42 projects across the waveguide, parallel to the bulkhead 26 and slightly above it. The pipette 42 may be constructed of glass and preferably has a 100 microliter capacity having an outer diameter of approximately 1.75 mm and an inner diameter of 1.48 mm; therefore the wall thickness of the pipette is only 0.27 mm. The end of the micropipette within the chamber is closed off by a brass cap 43. The other end of the micropipette projects through the wall of the waveguide so that samples may be introduced.

Biological samples, normally in vitro cells, are preferably suspended in a solution of the same phosphate buffered saline that is disposed within the waveguide chamber.

Since the micropipette 42 is a smooth cylinder having a diameter small compared to the wavelength of the incident radiation and since the solution that is used in the cell suspension medium is homogeneous with that in the chamber, the absorbed energy inside the pipette is also the same as that in the buffered solution.

Because the microwave field in a waveguide is determined, the power density of incident radiation and the rate of energy absorption can be readily calculated using measurements of the power meter 1.

The temperature of the cell suspension medium within the micropipette is the same as the temperature controlled medium within the chamber and accordingly the effects of radiation passing into the chamber upon the cells may be measured at a constant temperature.

The embodiments of the invention in which an exclusive property or privilege is claimed are defined as follows:

1. Apparatus for subjecting biological material to electromagnetic radiation, comprising: an electromagnetic radiation source; an elongated, hollow waveguide having one of its ends connected to the radiation source; a partition extending across the waveguide to form a chamber in the waveguide on the side of the partition opposite to that directed toward the radiation source; a liquid solution disposed in the chamber so as to extend fully across the waveguide; means for maintaining fluid within the chamber at a constant temperature; and a biological material container disposed within the chamber, said container having dimensions, in the direction of propogation of the radiation, which are sufficiently small compared to the wavelength of the radiation to prevent induction of the radiation within the container, whereby a biological sample disposed within the container is irradiated with radiation without appreciable heating.

2. The apparatus of claim 1 further including means associated with the waveguide for measuring the quantity of electromagnetic radiation impinging upon the chamber.

3. The apparatus of claim 1 in which said partition is formed of a material which matches the impedance of the chamber to the impedance of the waveguide to prevent any substantial reflection of radiation from the chamber toward the source.

4. The apparatus of claim 1 wherein said means for maintaining the liquid in the chamber at a constant temperature includes an exterior container for said liquid, means for circulating liquid between the exterior container and the chamber; and means for modifying the thermal content of the liquid in the container to maintain the liquid in the chamber at a constant temperature.

5. The apparatus of claim 4 wherein said means for maintaining the liquid in the container at a constant temperature includes means for measuring the temperature of the liquid in the chamber and for modifying the temperature of the liquid within the container as a function of said measured temperature.

6. The apparatus of claim 1 in which said biological material container comprises a glass pipette supported in one sidewall of the waveguide so as to project across the waveguide parallel to the partition.

7. The apparatus of claim 6 wherein said pipette has one end sealed and the other end passing through the wall of the waveguide.

8. The apparatus of claim 5 including means for measuring the level of liquid within the waveguide chamber and for controlling the exchange of liquid between the chamber and the exterior container to maintain a constant fluid level within said chamber.

9. The apparatus of claim 1 in which said radiation source generates microwave electromagnetic radiation and the waveguide has a rectangular cross-section.

10. The method of irradiating a biological sample with electromagnetic radiation without raising the temperature of the sample, comprising: placing the sample in an elongated container having a small cross-sectional dimension compared to the wavelength of the radiation, so that no radiation is induced into the container when the container is irradiated with the radiation; placing said container within a liquid chamber; passing radiation through the chamber in a direction transverse to the extension of the container; supporting the biological sample within the chamber in a liquid media substantially similar to the liquid in the container; and maintaining the liquid in the container at a constant temperature so that the biological specimen is maintained at said relative constant temperature while it is subjected to the radiation.

11. The method of claim 10 including the step of measuring the electromagnetic radiation incident upon said chamber.

12. Apparatus for irradiating living cells with microwave radiation without heating the cells, comprising: a microwave waveguide disposed with its central axis vertically; a microwave radiation source coupled to the bottom of the waveguide so as to project radiation upwardly therethrough, a partition extending across the waveguide; a body of fluid supported in the waveguide above the partition; a micropipette projecting through one wall of the waveguide above the partition, substantially across the width of the waveguide and adapted to support living cells in the same liquid contained in the waveguide chamber; and means for maintaining the liquid within the chamber at a constant temperature.

13. The apparatus of claim 12 wherein the liquid comprises a saline buffered solution.

14. The apparatus of claim 12 further including an exterior container for fluid, means connecting the exterior container to the volume in the waveguide above the partition; and means for pumping fluid between the waveguide and the container to maintain a constant liquid level within the chamber formed above the partition.

* * * * *

UNITED STATES PATENT AND TRADEMARK OFFICE
CERTIFICATE OF CORRECTION

PATENT NO. : 4,327,180
DATED : April 27, 1982
INVENTOR(S) : Chen, Kuo-Chun

It is certified that error appears in the above-identified patent and that said Letters Patent are hereby corrected as shown below:

Column 3, line 16 "1" should be --18--.

Signed and Sealed this

Seventeenth Day of August 1982

[SEAL]

Attest:

GERALD J. MOSSINGHOFF

*Attesting Officer*   *Commissioner of Patents and Trademarks*